United States Patent
Chaturvedi et al.

(10) Patent No.: US 11,597,731 B2
(45) Date of Patent: Mar. 7, 2023

(54) PROCESS FOR PREPARING HIGHLY PURE TEMOZOLOMIDE

(71) Applicants: Akshay Kant Chaturvedi, Bhiwadi (IN); Bijan Kumar Panda, Bhiwadi (IN); Amit Kumar, Bhiwadi (IN); Deepali Chaturvedi, Bhiwadi (IN)

(72) Inventors: Akshay Kant Chaturvedi, Bhiwadi (IN); Bijan Kumar Panda, Bhiwadi (IN); Amit Kumar, Bhiwadi (IN); Deepali Chaturvedi, Bhiwadi (IN)

(73) Assignee: SHIVALIK RASAYAN LIMITED, Rajasthan (IN)

( * ) Notice: Subject to any disclaimer, the term of this patent is extended or adjusted under 35 U.S.C. 154(b) by 0 days.

(21) Appl. No.: 17/378,663

(22) Filed: Jul. 17, 2021

(65) Prior Publication Data

US 2023/0041538 A1    Feb. 9, 2023

(51) Int. Cl.
   C07D 259/00    (2006.01)
   C07D 487/04    (2006.01)
   C07C 273/18    (2006.01)

(52) U.S. Cl.
   CPC ...... *C07D 487/04* (2013.01); *C07C 273/1854* (2013.01)

(58) Field of Classification Search
   CPC .................................................... C07D 259/00
   USPC ........................................................ 544/179
   See application file for complete search history.

(56) References Cited

U.S. PATENT DOCUMENTS

| | | | |
|---|---|---|---|
| 5,260,291 | A | 11/1993 | Lunt et al. |
| 6,844,434 | B2 | 1/2005 | Kuo |
| 7,087,751 | B2 | 8/2006 | Kuo et al. |
| 8,232,392 | B2 | 7/2012 | Turchetta et al. |
| 8,258,294 | B2 | 9/2012 | Pathi et al. |
| 2007/0225496 | A1 | 9/2007 | Palle et al. |

FOREIGN PATENT DOCUMENTS

WO    2010140168 A1    12/2010

OTHER PUBLICATIONS

Yongfeng Wang and Malcolm F. G. Stevens, Antitumor imidazotetrazines. 35. New synthetic routes to the antitumar drug temozolomide (Journal), May 5, 1997, 06 pages, J. Med. Chem. 1984,27,196-201, Nottingham, NG7 2RD, UK.
Yongfeng Wang and Malcolm F. G. Stevens, Antitumor imidazotetrazines. 35. New synthetic routes to the antitumar drug temozolomide (Journal), May 5, 1997, 07 pages, J. Org. Chem. 1997, 62, 7288-7294, Nottingham, NG7 2RD, UK.

*Primary Examiner* — Douglas M Willis

(57) ABSTRACT

The present invention provides a new process for preparation of imidazo-tetrazine class of chemical entity useful as anticancer agent. The present invention provides a commercially and economically viable process for preparation of Temozolomide of formula (VI).

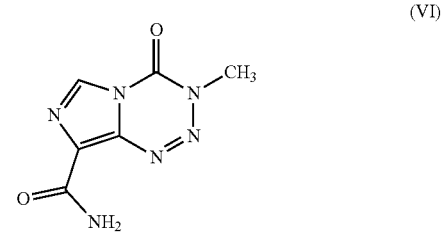

Present invention also relates to an intermediate compound of formula (III) and its preparation useful in the process for preparing Temozolomide.

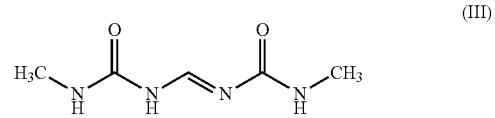

6 Claims, 3 Drawing Sheets

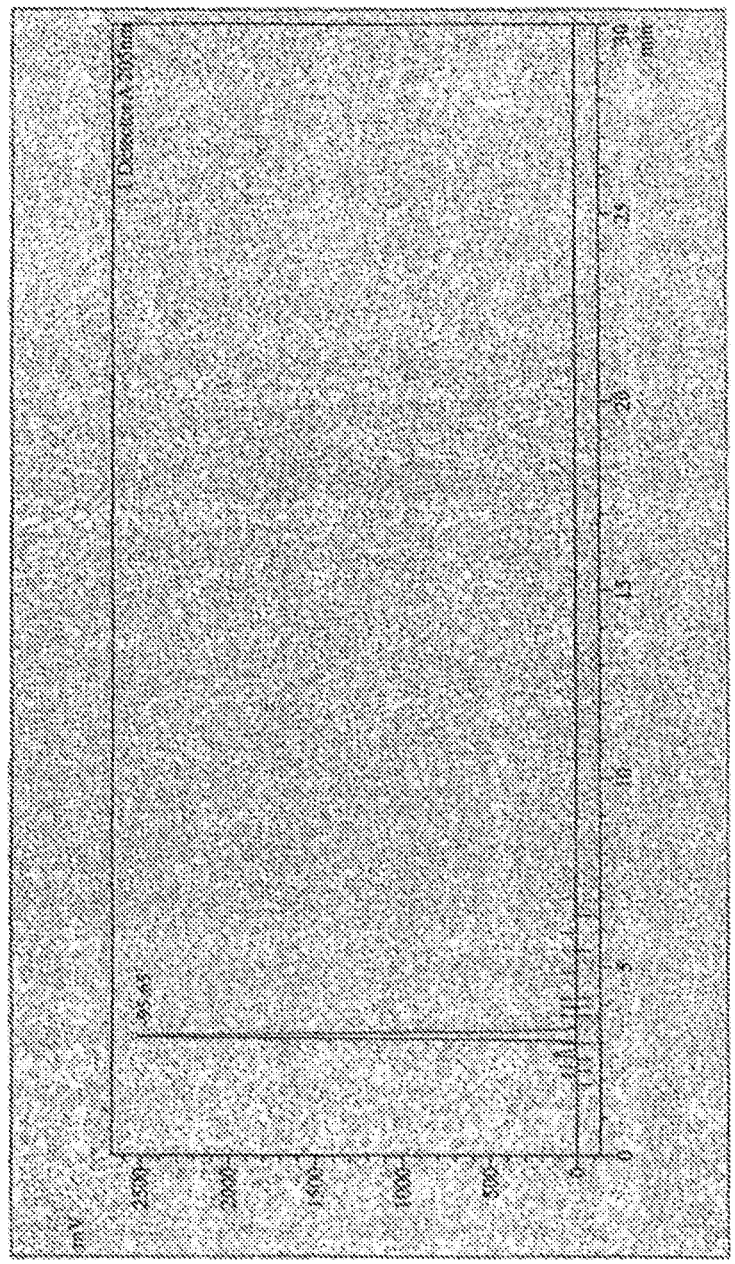

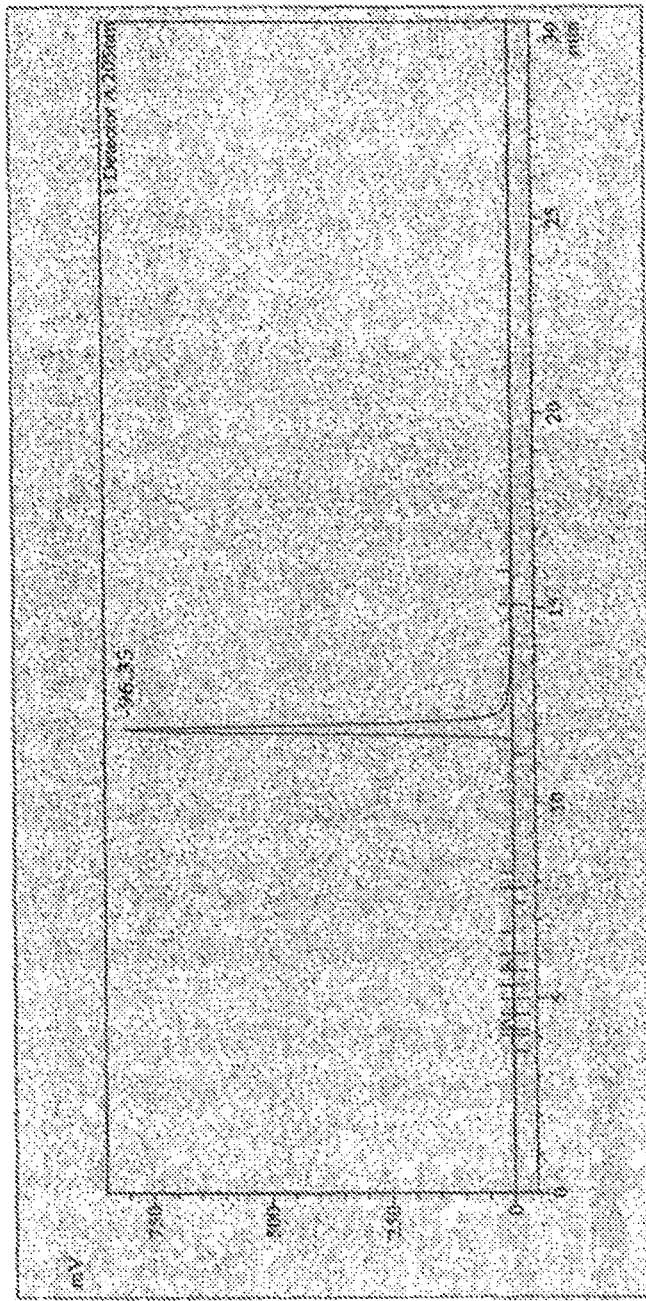

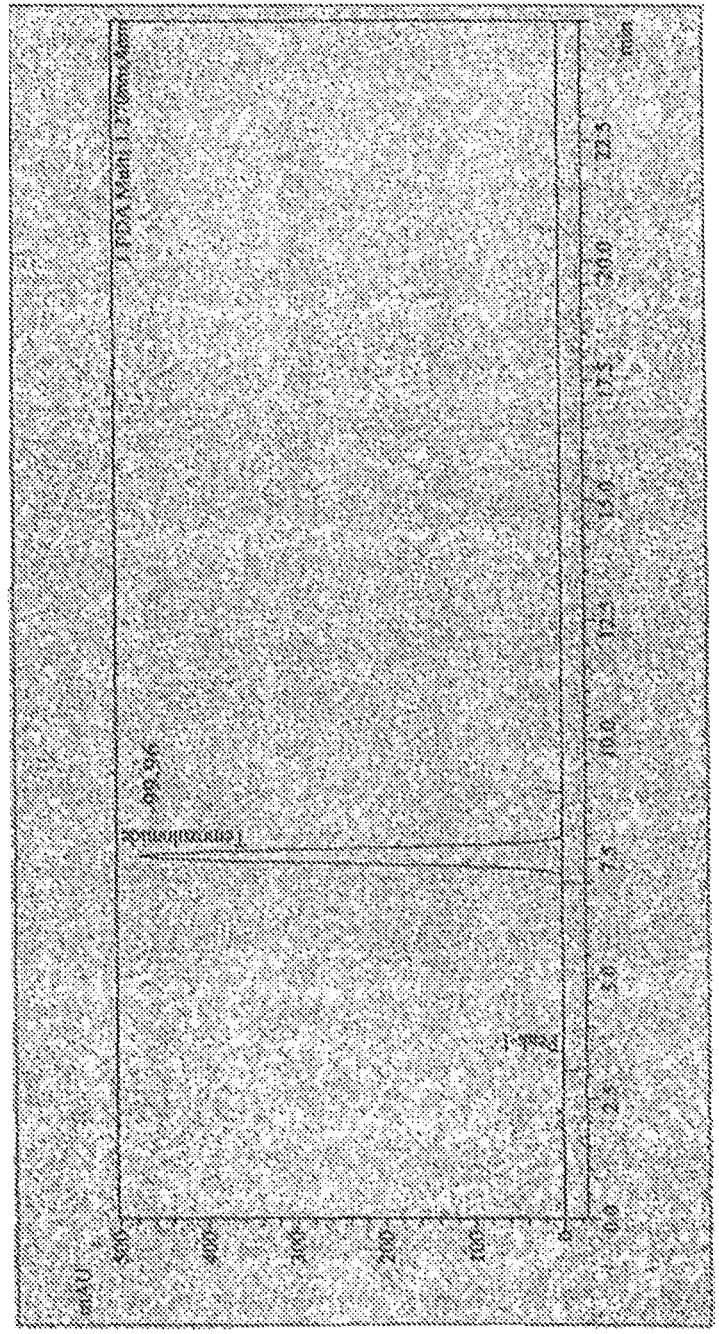

PROCESS FOR PREPARING HIGHLY PURE TEMOZOLOMIDE

FIELD OF THE INVENTION

The present invention relates to improved and industrially viable process for the preparation of highly pure Temozolomide (VI) and its intermediate compound of formula (III).

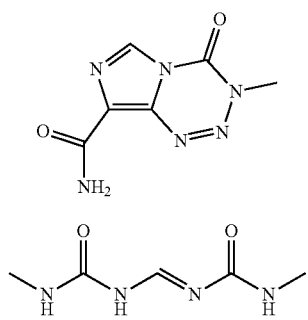

BACKGROUND OF THE INVENTION

Temozolomide, also known as 3-methyl-8-aminocarbonyl-imidazo[5,1-d]-1,2,3,5-tetrazin-4(3H)-one is a known antitumor drug, and is represented by formula VI:

(VI)

It is indicated for treating patients with malignant glioma such as cancer, refractory anaplastic, astrocytoma, i.e. patient at first relapse who have experienced disease progression in malignant glioma, glioblastoma multiform and anaplastic astrocytoma, on a drug containing a nitrosourea and procarbazine. It is sold in the US market as oral capsules dosage forms containing 5 mg, 20 mg, 100 mg, 140 mg, 180 mg or 250 mg as Temodar® by Schering Corporation.

J. Med. Chem. 1984, 27, 196-201 describes a process wherein 5-amino-1H-imidazole-4-carboxamide is converted into 5-diazo-1H-imidazole-4-carboxamide, which is then cyclised with methylisocyanate in dichloromethane to provide Temozolomide.

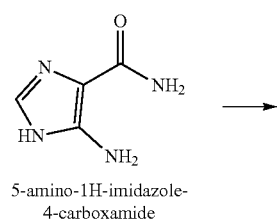

5-amino-1H-imidazole-
4-carboxamide

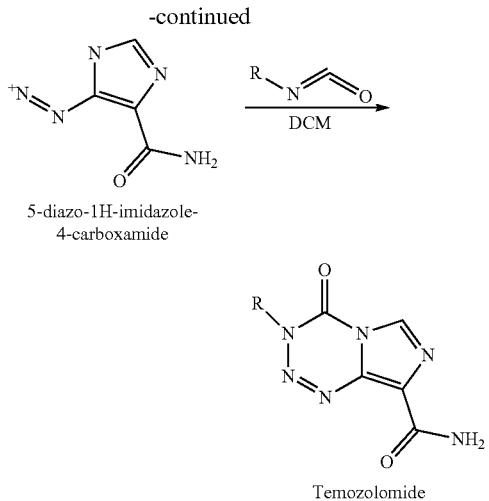

This process requires isolation of the unstable and potentially dangerous 5-diazo-1H-imidazole-4-carboxamide. Methyl isocyanate is another difficult reagent to handle and transport, especially on the industrial scale. Further, the cyclization using methylisocyanate also requires a long reaction time with large number of impurities formation.

J. Org. Chem. 1997, 62, 7288-7294 describes a process for preparing Temozolomide wherein the last step of diazotization results equi-formation of aza-hypoxanthine dye and temozolomide, resulting in poor yield. This literature does not provide the complete details of the experimental procedure for work up.

Edward et al in U.S. Pat. No. 5,260,291 first generically discloses the product Temozolomide and its derivatives as per Scheme-1

Scheme-1: as per US5260291A

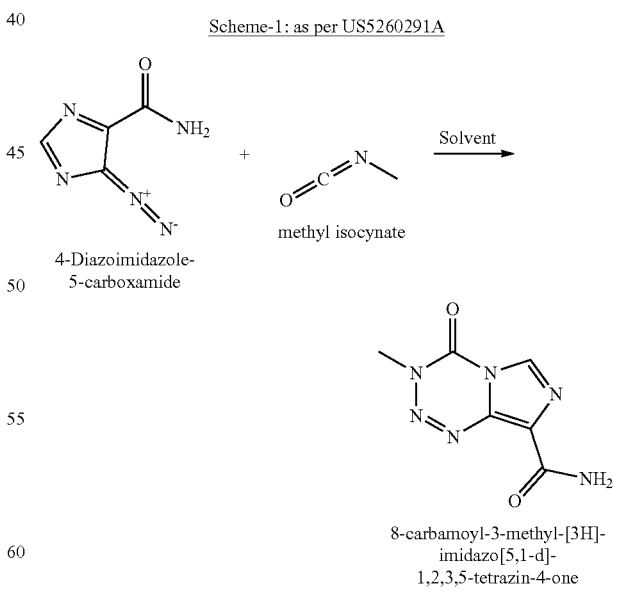

In this patent, the process results in the poor yield due to the decomposition of Temozolomide to impurities like compound of formula 5-(3-methyltriazen-1-yl) imidazole-4-carboxamide (VII)

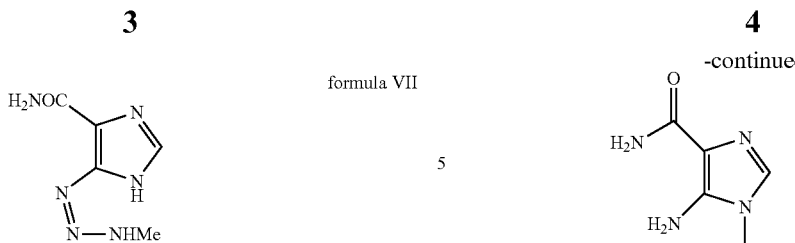

formula VII and 5-amino-1H-imidazole-4-carboxamide. Further the reactant methyl isocyanate is not safe to handle in the industrial/lab purpose.

Shen-Chun et al in U.S. Pat. No. 6,844,434 describes a process involving the use of a bulky protecting group on nitrogen of the primary amide for cyclisation in presence of LiCl to minimize the undesired cyclization product. After cyclization the protecting group has to be removed, which makes the process more laborious with more number of steps as depicted in the below mentioned Scheme-2:

Scheme-2: as per US6844434

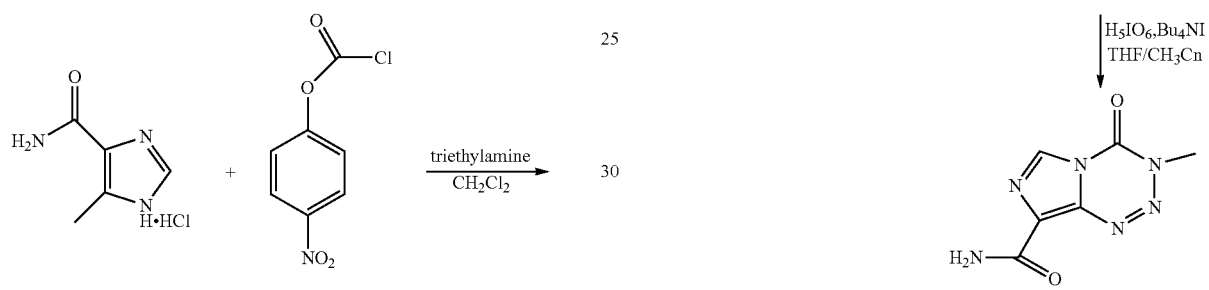

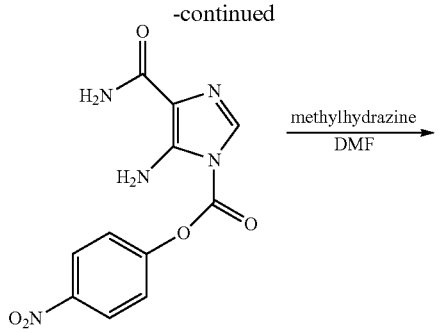

Scheme-3: as per US7087751B2

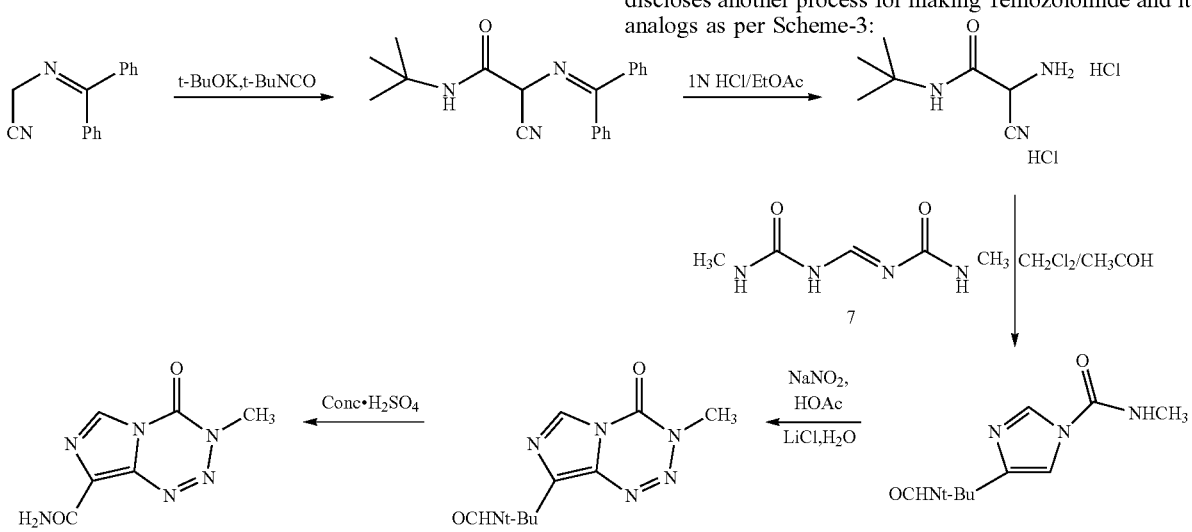

Shen-Chun et al in U.S. Pat. No. 7,087,751 generically discloses another process for making Temozolomide and its analogs as per Scheme-3:

Synthesis of the Temozolomide described in this patent consists of a high number of synthetic steps and the involvement of a dangerous reactant such as t-butylisocyanate resulting the process to be non-amenable to scale up for industrial synthesis.

Raghavendracharyulu venkata et al in US20070225496 discloses the synthesis of Temozolomide as per scheme 4:

Scheme-4: as per US2007/0225496

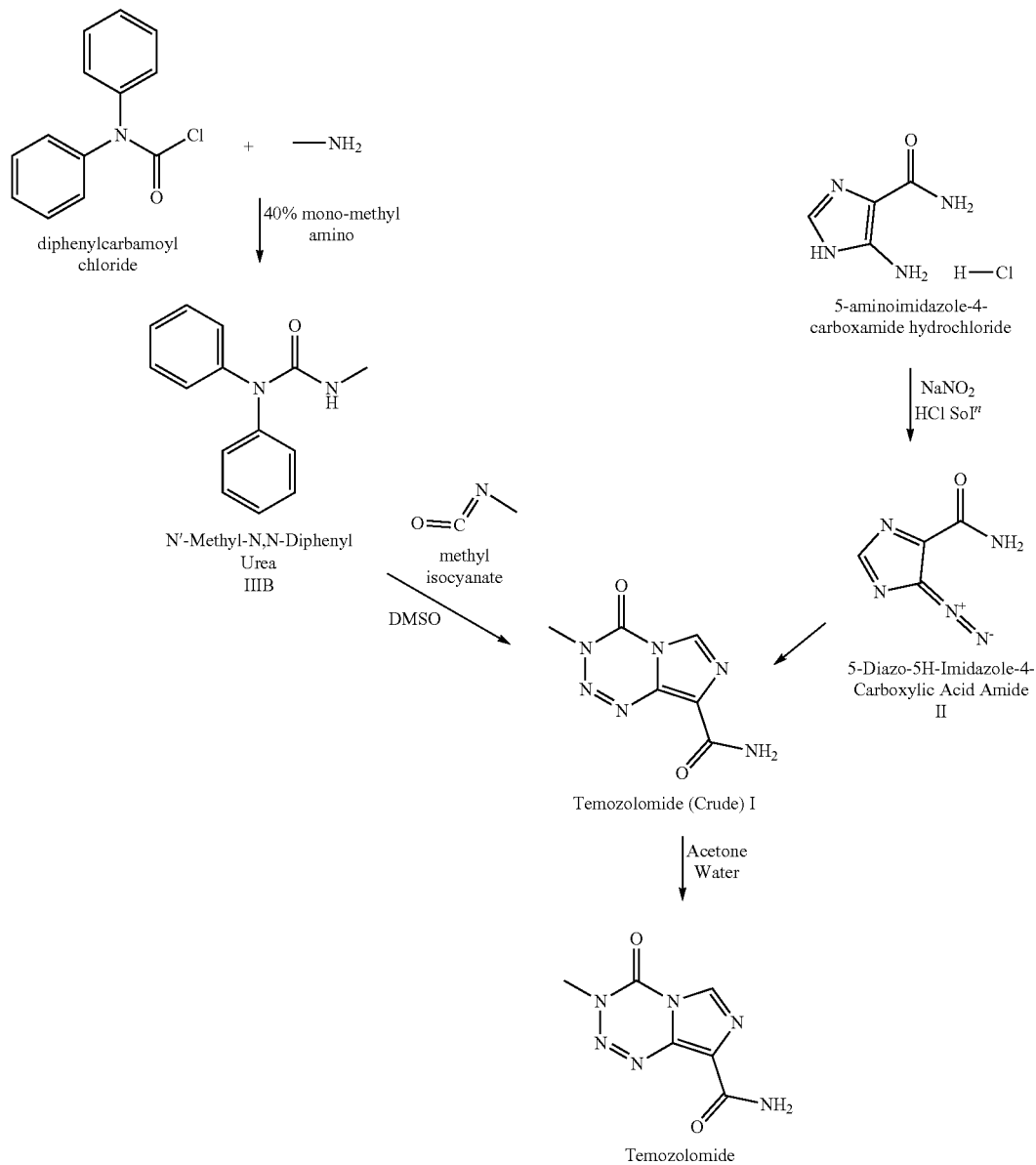

The above described process involves use of methyl isocyanate, which is highly flammable and difficult to handle on large scales that make the process unsuitable for industrial synthesis. In addition to this, isolation of Temozolomide from the reaction mixture requires addition of large amount of ethyl acetate followed by addition of hexane and again ethyl acetate to isolate the compound.

Bhirud et al in WO20100140168 discloses a process for preparation of Temozolomide as per Scheme 5:

Scheme -5: as per WO20100140168A1

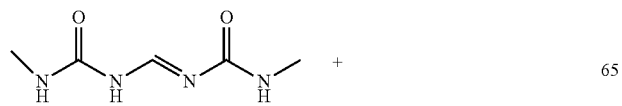

-continued

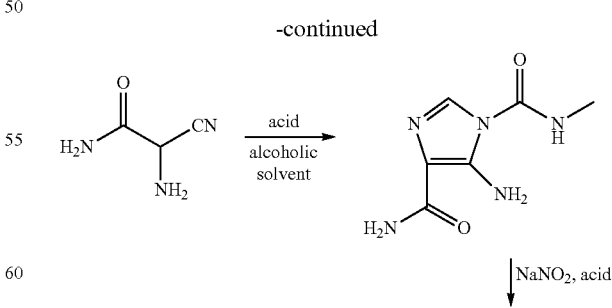

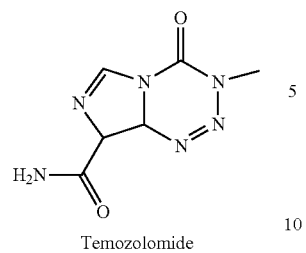

Temozolomide

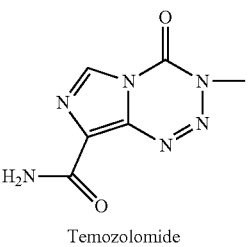

Temozolomide

The process involves the necessarily use of alcoholic solvent, which was found to result in loss of intermediate yield besides more time consuming steps owing to impurities formation leading to an intermediate of purity about 90-95% (area % by HPLC). The process also involves use of organic acid as acetic acid as necessary requirement, however, inventors observed that said reaction was surprisingly found to run smooth while using hydrochloric acid or like mineral acids. A reproduction of the industrially amenable process was also found difficult owing to inconsistencies/variability in the steps due to impurities formation. Hence, inventors of the present application observed that many improvements are possible in the process to make the process not only economically viable & robust, but also easily amenable to scale up with green chemistry compliance.

Turchetta et al in U.S. Pat. No. 8,232,392 discloses the synthesis of Temozolomide by the addition of 5-aminoimidazole-4-carboxamide and N-succinimidyl-N'-methyl carbamate and further the cyclization of caramoyl-5-amino imidazole-4-carboxamide.

The process involves purification of Temozolomide by means of Column chromatography on adsorbent polymeric resin, which is considered to be tedious and more time consuming process and hence industrially not applicable.

S L Pathi et al in U.S. Pat. No. 8,258,294 discloses the synthesis of Temozolomide as per Scheme-7:

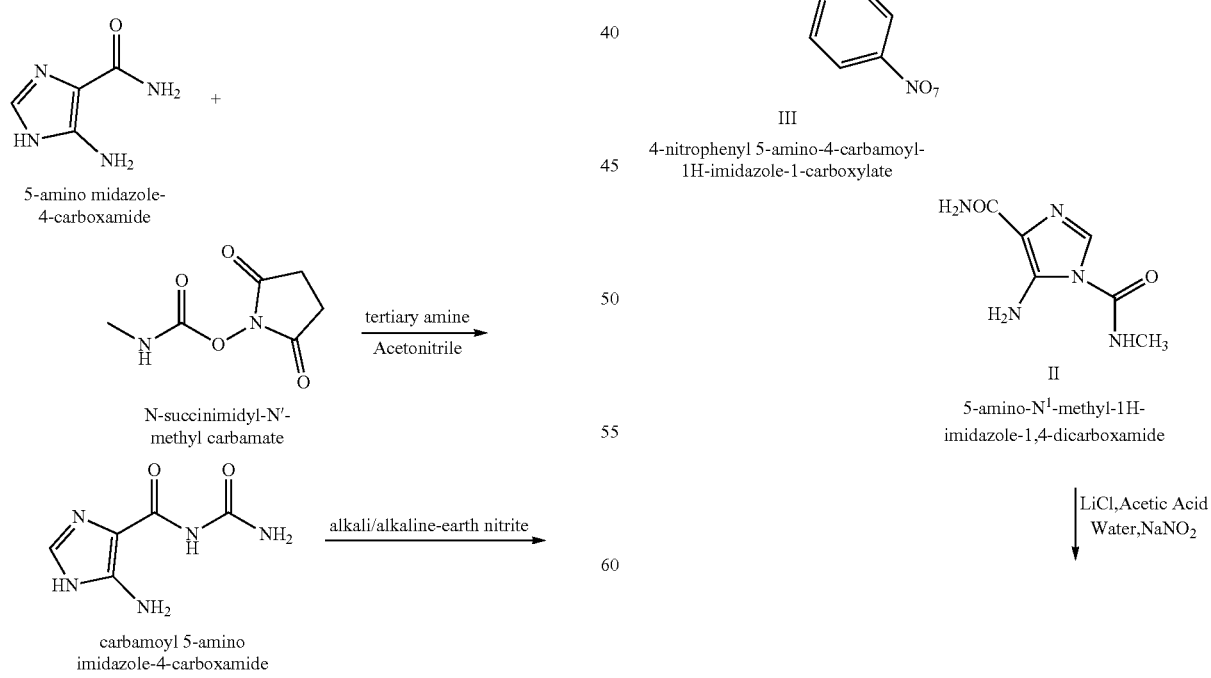

-continued

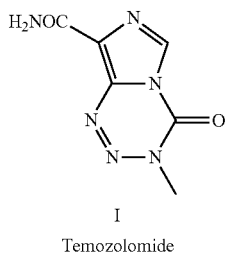

isolation by the continuous liquid-liquid extration technique by using the water-immiscible solvent ←

I
Temozolomide

This process involves the counter current continuous liquid-liquid extraction technique to isolate Temozolomide.

Patent application describes two methods for the extraction of Temozolomide.

In first method, Temozolomide is extracted from the reaction mixture by counter current extraction using continuous liquid-liquid extractor. Although the use of countercurrent extraction reduces the usage of solvent during extraction but isolation requires a specific apparatus. The use of tedious step of counter current extraction and need of the specific apparatus makes the process unsuitable from the industrial point of view.

In the second method, Temozolomide is extracted using conventional techniques which requires large volumes of solvent such as dichloromethane (1000 times) with respect to the starting imidazole intermediate to obtain reasonable amount of crude Temozolomide which needs further two or three times crystallization to achieve desired purity. The process is not industrially viable and product cannot be extracted effectively due to handling problem of huge volumes of solvent.

Other patent application viz; WO2018112589, WO2018122724, IN162/MUM/2012 and CN103626772 also discloses the processes for making Temozolomide, however they result in one or the other difficulties of industrial up scalability more particularly the poor yields, large number of impurities formation, multiple steps of isolation, size of equipment etc. Space has to be taken in to account, because use of such large reactors (for distillation) and specific apparatus for the extraction like liquid-liquid extractor, as reported in prior art, and handling of hazardous reagents resulting in the need of developing an industrial viable process.

Due to the existing difficulties in the prior art disclosed process, there still exist need to develop a process for preparing Temozolomide which is more convenient, especially on an industrial scale, to provide improved yields and purity.

Thus, present invention fulfils the need of the art and provides an improved and industrially applicable process for the preparation of Temozolomide.

BRIEF SUMMARY OF THE INVENTION

Particular aspects of the present application relate to the process for preparation of highly pure Temozolomide (VI). The application further relates to processes for preparation of an intermediate compound of formula (III) useful in the process for preparing Temozolomide. Temozolomide (VI) obtained by the process according to the present invention is useful in the treatment of cancer.

Different aspects of the present application are summarized herein below individually.

In one aspect of the present application, the present invention relates to a process for preparation of highly pure Temozolomide (VI)

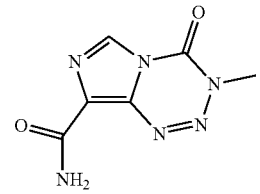

(VI)

comprising the steps of:

a) reacting the compound of formula (I) and (II)

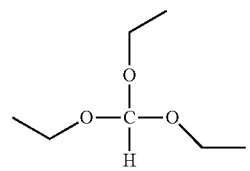

(I)

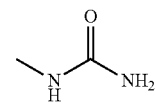

(II)

at temperature ranging between 100-120° C. for time duration ranging between 4-10 hrs to get the compound of formula (III);

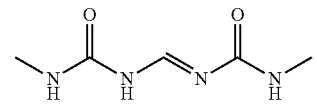

(III)

b) reacting the compound of formula (III) and (IV);

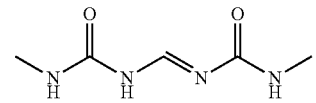

(III)

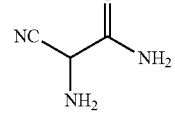

(IV)

in the presence of a non-alcoholic solvent and an inorganic acid to get the compound of formula (V);

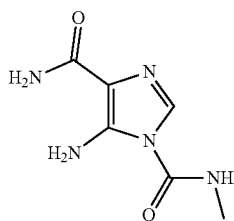

(V)

c) reacting the compound of formula (V) with an organic acid (C1-C3) and sodium nitrite in aqueous medium at temperature ranging between −5° C. to 10° C. followed by addition of desiccant in the quantity ranging between 20-40% w/w with respect to the total quantity used as aqueous medium to get Temozolomide; and d) insitu purifying Temozolomide by using 4 to 10% w/w DMSO solution in halohydrocarbon to get the highly pure Temozolomide of formula (VI).

In another aspect of the present invention, it relates to the process for purification of compound of formula (III) comprising the steps of:

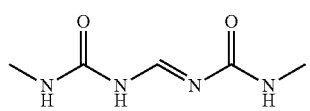

(III)

a) reacting the compound of formula (II) with the compound of formula (I);

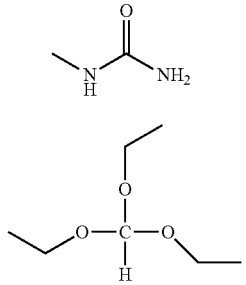

(II)

(I)

b) raising the temperature to a range between 100-120° C.;
c) maintain the reaction temperature for time duration ranging between 4-10 hrs;
d) cooled the reaction mixture for temperature ranging between −5 to 10° C.;
e) optionally washing the precipitate with an organic solvent; and
f) isolating the compound of formula (III).

In yet another aspect according to the present invention it relates to highly pure Temozolomide having purity of greater than 99.8% (by HPLC).

Further particular aspects of the invention are detailed in the description part of the specification, wherever appropriate.

BRIEF DESCRIPTION OF THE DRAWINGS

FIG. 1 is an illustration of HPLC graph of compound of formula (III). (Example: 2)

FIG. 2 is an illustration of HPLC graph of compound of formula (V). (Example: 3a)

FIG. 3 is an illustration of HPLC graph of compound of formula (VI) i.e. Temozolomide. (Example: 4)

DETAILED DESCRIPTION OF THE INVENTION

As set forth herein, embodiments of the present invention relate to a process for preparation of highly pure Temozolomide (VI). The present invention deals with a simple and industrially efficient process for making the compound of formula (III), which exhibits various advantages over other ways of conversion known in the art. The advantages are discussed on the relevant places of further description. Individual embodiments of the present invention are detailed herein below separately.

In one embodiment according to the present application, it provides a process for preparing Temozolomide (VI).

In an embodiment of the present application, it provides a process for preparation of Temozolomide (VI), (VI)

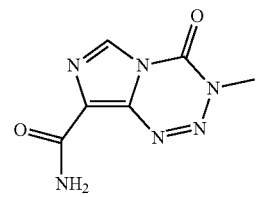

comprising the steps of:
a) reacting the compound of formula (I) and (II)

(I)

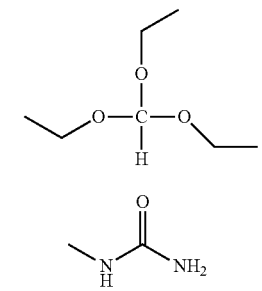

(II)

at temperature ranging between 100-120° C. for time duration ranging between 4-10 hrs to get the compound of formula (III);

(III)

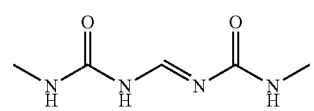

b) reacting the compound of formula (III) and (IV);

(III)

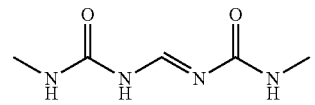

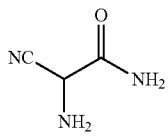
(IV)

in the presence of a non-alcoholic solvent and an inorganic acid to get the compound of formula (V);

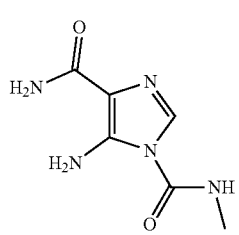
(V)

c) reacting the compound of formula (V) with an organic acid (C1-C3) and sodium nitrite in aqueous medium at temperature ranging between −5° C. to 10° C. followed by addition of desiccant in the quantity ranging between 20-40% w/w with respect to the total quantity used as aqueous medium to get Temozolomide; and d) in-situ purifying Temozolomide by using 4 to 10% w/w DMSO solution in halohydrocarbon to get the highly pure Temozolomide of formula (VI).

Individual steps of the embodiments are detailed herein below.

In process for the preparation of Temozolomide in step b) non-alcoholic solvent is selected from dichloromethane, dichloroethane, toluene and acetonitrile or a mixture thereof.

The process step b) is carried out in the presence of an inorganic acid selected from the hydrochloric acid, sulphuric acid, nitric acid or a combination thereof.

In one of the particular embodiment according to present invention inorganic acid in the process step b) is hydrochloric acid.

The process step b) is performed at 20-25° C. (RT) in inorganic acid and nonalcoholic solvent over a period of about 18 hours.

The process step c) is carried out in the presence of an organic acid ($C_1$-$C_3$).

In one of the particular embodiment according to present invention C1-C3 organic acid selected from formic acid, acetic acid, propanoic acid or a mixture thereof.

In further embodiment according to present invention, acid in the process step c) is acetic acid.

In still another embodiment according to the present invention, source of nitrous in the process step c) is nitrous acid.

In yet further embodiment according to the present invention the process step c) at temperature ranging between −5° C. to 10° C.

In one of the particular embodiment according to present invention the process step c) was performed ranging between −5° C. to 0° C.

In further embodiment according to present invention the source of desiccant used in the process step c) for the preparation of Temozolomide is selected from sodium dithionate, sodium sulphate, barium chloride and calcium chloride.

In one of the particular embodiment according to present invention the source of desiccant used in the process step c) is calcium chloride.

In yet further embodiment according to the present invention the process step d) is carried out in the presence of 4 to 10% w/w DMSO solution in halohydrocarbon solvent, which may be carried out suitably either insitu or by isolating the wet crude and further performing the addition in 4-10% DMSO solution in halohydrocarbon solvent.

Inventors of the present application found that use of 4-10% DMSO solution in halohydrocarbon was found to be useful to get the highly pure Temozolomide. A lesser amount of DMSO i.e. 1-2% solution was found to result in the Temozolomide as lesser pure as compared to 4-10% DMSO solution.

The larger amount of polar and colour impurities (resulting due to dye formation during diazotization stage) were found to get trapped owing to DMSO presence in halohydrocarbon solvent.

In yet further embodiment according to the present invention the process step d) is carried out in the presence of halohydrocarbon selected from dichloromethane, chloroform, carbon tetrachloride or a combination thereof.

In one of the particular embodiment according to present invention the source of halo-hydrocarbon solvent used in the process step d) is dichloromethane.

In a particular preferred embodiment according to the present process, the purification was performed insitu i.e. without isolation of any crude and performing purification as such to avoid multistep operations and minimize the overall reaction time.

The process for preparing the compound of formula (III) comprising the steps of:

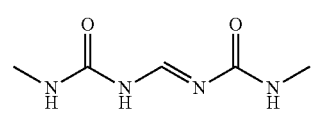
(III)

a) reacting the compound of formula (II) with the compound of formula (I).
b) raising the temperature to a range between 100-120° C.;
c) maintain the reaction temperature for time duration ranging between 4-10 hrs;
d) cooled the reaction mixture for temperature ranging between −5 to 10° C.;
e) optionally washing the precipitate with an organic solvent; and
f) isolating the compound of formula (III).

The process step b) is performed at temperature range between 100-120° C. preferably at 120° C. In one embodiment according to the present invention the process step c) is carried out to maintain the reaction temperature for time duration ranging between 4-10 hrs.

In one of the particular embodiment according to present invention the process step c) is performed for 10 hours.

Optionally the precipitate obtained according to present invention in the process step d) the source of suitable organic solvents that can be used in the process step e) is selected from dichloromethane, chloroform, carbon tetrachloride, ethylacetate or a combination thereof.

The product which is in the form of precipitate can be isolated by suitable methods such as filtration or centrifugation and then dried.

In yet further embodiment according to the present invention the process step f) the compound of formula (III) having the purity greater than 95% (by HPLC).

Temozolomide obtained from the present invention is highly pure and free from undesired impurities. Temozolomide, thus obtained having the purity of greater than 99% and more preferably 99.9% (by HPLC).

The purification process can be repeated with same or different solvent till the Temozolomide of desired purity is obtained. Temozolomide obtained from the present invention is highly pure and free from undesired impurities.

A solid pharmaceutical composition of Temozolomide comprising highly pure Temozolomide according to the process of present invention may be a capsule or tablet or in granules form or injectable composition. The composition may be prepared by conventional formulation methods as per the requirements. The readily dispersible may be also developed in the form of a solution suitable for oral administration or can be in granules form. The composition comprises granules of Temozolomide and a dispersant.

The granules are prepared by mixing the Temozolomide with one or more emulsifiers and optionally one or more adsorbents.

Suitable emulsifiers include, but are not limited to, sodium lauryl sulfate, poloxamer, saturated polyglycolized glyceride (so-called Gelucire), labrasol, polysorbates (such as polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80)), sorbitan esters (such as sorbitan monolaurate (Span 20), sorbitan monopalmitate (Span 40), sorbitan monostearate (Span 60), sorbitan monooleate (Span 80), sorbitan trilaurate (Span 25), sorbitan trioleate (Span 85) and sorbitan tristearate (Span 65)), cremophor (e.g., Cremophor EL), PEG-60 hydrogenated castor oil, PEG-40 hydrogenated castor oil, sodium lauryl glutamate, disodium cocoamphodiacetate, tyloxapol, lauroyl macrogol-6 glycerides (Labrafil M2130CS=lauroyl polyoxyl-6 glycerides), oleoyl macrogol-6 glycerides (Labrafil M1944CS), linoleoyl macrogol-6 glycerides (Labrafil M2125 CS=linoleoyl polyoxyl-6 glycerides), propylene glycol monocaprylate (Capryol 90), propylene glycol monocaprylate (Capryol PGMC), propylene glycol monolaurate (such as type II (Lauroglycol 90) or type I (Lauroglycol FCC), polyglyceryl-3 dioleate a oleate (Plurol Oleique CC 497). triglycerides medium-chain (e.g. C8 and C10) (such as Labrafac Lipophile WL 1349), propylene glycol dicaprylocaprate (Labrafac PG), diethylene glycol monoethyl ether (Transcutol), behenoyl polyoxyl-8 glycerides or PEGylated glyceryl behenate (Compritol HD5 ATO), glyceryl behenate (Compritol 888 Pellets), glyceryl dipalmitostearate (Biogapress Vegetal BM297ATO), glyceryl behenate E471 (Compritol E ATO), a mixture of (i) refined soybean oil, (ii) glyceryl distearate and (iii) polyglyceryl-3 dioleate (Geloil SC), diethylene glycol monoethyl ether (Transcutol V), octylphenol ethoxylate (Triton X-100), and sodium deoxycholate. A preferred emulsifier is stearoyl macrogol-32 glycerides (available as Gelucire 50/13 from Gattefosse of Paramus, N.J.). Suitable adsorbents include, but are not limited to, talc, fumed silica, colloidal silicon dioxide, calcium silicate, microcrystalline cellulose, and aluminum magnesium metasilicate. A preferred adsorbent is colloidal silicon dioxide.

The granules can be prepared by melting the emulsifier (e.g., stearoyl macrogol-32 glycerides) (e.g., at 50° C.), adding the Temozolomide and mixing to uniformity while maintaining the heat, allowing the mixture to harden, optionally breaking the mixture into smaller pieces (e.g., using a high shear granulator and then a jet mill), and granulating the mixture, optionally with one or more adsorbents.

The granules are coated to provide taste masking, safety in case the granules spill and the desired release profile upon oral administration. The coating provides a barrier permitting safe handling of the composition and preventing a patient from the toxic effects of skin contact of Temozolomide.

Coating materials include, but are not limited to, methacrylate-based polymers, such as cationic polymers with a dimethylaminoethyl ammonium group (e.g., Eudragit® E PO available from Evonik Industries of Darmstadt, Germany). A preferred pH dependent coating material is amino methacrylate copolymer (e.g., Eudragit® E 100 available from Evonik Industries of Darmstadt, Germany). The pH dependent coating material can be a pH sensitive cationic coating material, such as polyvinylacetal diethylaminoacetate (AEA), acrylamide, aminoethyl methacrylate, N,N'-dimethylaminomethylacrylamide, N,N'-dimethylaminoethyl methacrylate, N,N'-dimethylaminopropyl methacrylate, N,N'-diethylaminoethyl methacrylate, diallyldimethylammonium chloride, and cationic polymers from natural sources (such as polylysine, polyhistidine, and chitosan).

The coating composition can be sprayed onto the Temozolomide granules by using a fluidized bed granulator (using, for example, a top spray). Preferably, the spraying is performed at a temperature of about 25° C. to about 40° C.

The final solid pharmaceutical preparation can be prepared by mixing the coated granules with one or more dispersants and optionally other components, such as sweeteners, glidants, lubricants, and flavours.

Suitable dispersants include, but are not limited to, crospovidone. Pharmasperse® 416, isomalt, maltodextrin, mannitol, maltose, sorbitol, and maltitol, one preferred dispersant is Pharmasperse® 416 (available from SPI Pharma, Inc. of Wilmington, Del.), which contains 49.3-69.3% polyol (on a dry basis) and 30.4-50.4 calcium carbonate and has a tapped density of 0.59-0.75 g/mL and a bulk density of 0.52-0.68 g/mL.

Suitable sweeteners include, but are not limited to, sucralose, sodium saccharin, aspartame, and neutrame. The amount of sweeteners can range from about 0% to about 2%, such from about 0.1 to about 0.5%, based upon the total weight of the solid pharmaceutical composition. Suitable glidants include, but are not limited to, talc, fumed silica, colloidal silicon dioxide, magnesium stearate, stearic acid, kaolin, and magnesium trisilicate.

Suitable lubricants include, but are not limited to, magnesium stearate. The amount of lubricants can range from about 0.1% to about 1%, such from about 0.2 to about 0.5%, based upon the total weight of the solid pharmaceutical composition.

Suitable flavours include natural and artificial powdered flavours. The amount of flavours can range from about 0% to about 4%, such from about 1 to about 3%, based upon the total weight of the solid pharmaceutical composition.

The solid pharmaceutical composition or Temozolomide powder of the present invention may be administered by measuring an appropriate or desired dose of the solid pharmaceutical composition or Temozolomide powder with a measuring device, and then administering (e.g., by the oral route) the dose.

The powder can be packaged in a high density polyethylene (HDPE) container. The powder can be dispensed and administered with a dosing syringe, scoop, or a cap (e.g., a cap of a bottle or jar such as one fitted with a fill-to line).

The invention is further defined by reference to the following examples describing in detail by the preparation of the compounds of the invention. It will be apparent to those skilled in the art that many modifications, both to materials and methods, may be practiced without departing from the scope of the invention.

EXAMPLES

The process for preparation of highly pure Temozolomide (VI) according to the present invention is a multistep procedure, which is detailed in the stepwise demonstration mentioned herein below:

Stage-1: Preparation of Aminocyanoacetamide

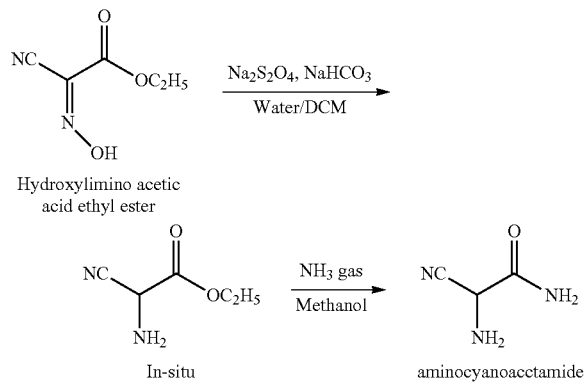

Hydroxylimino acetic acid ethyl ester

To a solution hydroxylaminocyano acetic acid ethyl ester (30.0 g, 0.21 mol.) was dissolved in saturated solution of sodium bicarbonate (90 ml) and water (180 ml) and then added portion wise Sodium dithionite (102 g, 0.59 mol.). The resulting mixture was stirred at 25-30° C. for 45 min. After reaction completion product extracted with DCM (200 ml×4). Whole DCM layer were combined and washed with saturated brine solution (200 ml) and concentrated organic layer under vacuum to get oily mass. Charge methanol and in methanol (150 ml) was added to the residue and distilled out under vacuum to remove traces of DCM. Added 8% methanolic ammonia (220 ml) in the residue and purged ammonia gas in reaction mass for 15 min and reaction progress checked by TLC. After reaction completion removed methanol under vacuum till material precipitation cooled up to 0-5° C. and filtered the mass after 60 min stirring. Washed wet cake with 100 ml chilled methanol. Dried at 40-45° C. to get title compound 4.2 g.
Purity (by HPLC): 99.6%.

Stage 2: Preparation of 1-methyl-3-methylcarbamoyliminomethyl urea

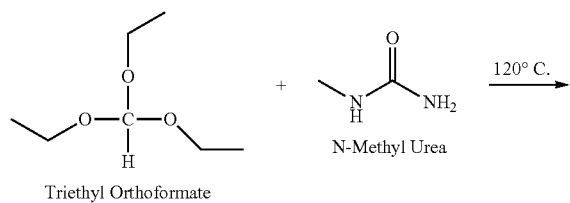

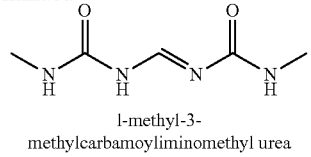

1-methyl-3-methylcarbamoyliminomethyl urea

A suspension of monomethyl urea (50 g, 0.67 mol.) in tri ethyl orthoformate (150 ml, 0.90 mol.) was heated to reflux at 120° C. bath temperature and internal temperature 100° C. for 10 hrs. Reaction progress checked by HPLC. After reaction completion the reaction mixture was cooled to 5-10° C., and stirred for 1 hour to ensure complete precipitation, of the product. The resulting solid was filtered, washed with ethyl acetate (25 ml) and dried under vacuum at 45-50° C. to yield 35 g (65%) of title compound.
Purity (by HPLC): 95.66%.

Stage 3: Preparation of 5-amino-N1-methyl-1H-imidazole-1,4-dicarboxamide

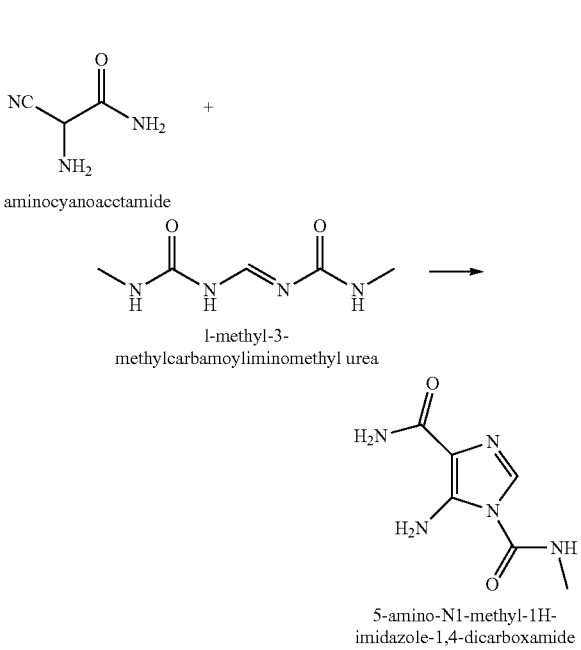

3a) Conc. HCl (1.2 g, 12 m. mol) was added to a suspension of amino cyanoacetamide (10 g, 100 m mol) and 1-methyl-3-methylcarbamoyliminomethyl urea (19 g, 120 m mol) in Acetonitrile (54 ml) at 20-25° C. and the mixture was stirred at 20-25° C. for 24 hours till completion of the reaction (monitored by HPLC). The reaction mixture was distilled up to 50% approx. of acetonitrile used, cooled to 0-5° C., stirred for 1 hour and the resulting solid was filtered, washed with 20 ml chilled acetonitrile, suck dried and finally dried under vacuum at 30-35° C. to afford 16.3 g (90.5%) of title compound as an off white colored solid.
Purity (by HPLC): 98.35%.

3b) Hydrochloric acid (0.6 g, 5.9 m. mole) was added to a suspension of amino cyanoacetamide (5 g, 50.4 m. mole) and 1-methyl-3-methylcarbamoyliminomethyl urea (9.48 g, 59.9 m. mole) in Methanol toluene mixture (50.0 ml and 25 ml each) at 20-25° C. and the mixture was stirred at 20-25°

C. for 18 hours till completion of the reaction (monitored by TLC). The reaction mixture was cooled to 0-5° C., stirred for 1 hour and the resulting solid was filtered, washed with chilled methanol toluene mixture (8 ml, 4 ml each), suck dried and finally dried under vacuum at 30-35° C. to afford 5.7 g (62.0%) of title compound as an off white colored solid.

Purity (by HPLC): 99.07%.

3c) Hydrochloric acid (0.6 g, 5.9 m. mole) was added to a suspension of amino cyanoacetamide (5 g, 50.4 m. mole) and 1-methyl-3-methylcarbamoyliminomethyl urea (9.48 g, 59.9 m. mole) in DCM (50.0 ml) at 20-25° C. and the mixture was stirred at 20-25° C. for 18 hours till completion of the reaction (monitored by TLC). The reaction mixture was cooled to 0-5° C., stirred for 1 hour and the resulting solid was filtered, washed with chilled DCM (8 ml,), suck dried and finally dried under vacuum at 30-35° C. to afford 12.6 g crude STE 02 light yellow powder, which was purified in 60 ml methanol and 6 ml acetic acid mixture and stirred for 5 hrs. at room temperature and cooled up 0.5° C. for 1 hr. filtered and washed with chilled methanol (10 ml). Dried at 30-35° C. for 6 hrs to get off white powder 7.8 g.

Purity (by HPLC): 98.74%

Reference Example for the preparation of 5-amino-N1-methyl-1H-imidazole-1,4-dicarboxamide: (WO2010/140168) Acetic acid (15 ml, 0.26 mol) was added to a suspension of amino cyanoacetamide (30 g, 0.30 mol) and 1-methyl-3-methylcarbamoyliminomethyl urea (57 g, 0.36 mol) in methanol (150.0 ml) at 20-25° C. and the mixture was stirred at 20-25° C. for 18 hours till completion of the reaction (monitored by HPLC). The reaction mixture was cooled to 0-5° C., stirred for 1 hour and the resulting solid was filtered, washed with chilled methanol (450 ml), suck dried and finally dried under vacuum at 30-35° C. to afford 42 g (77.7%) of title compound as an off white colored solid.

Purity (by HPLC): 92.21% (After re-purification, purity achieved 99.21% HPLC).

Stage 4: Preparation of Temozolomide

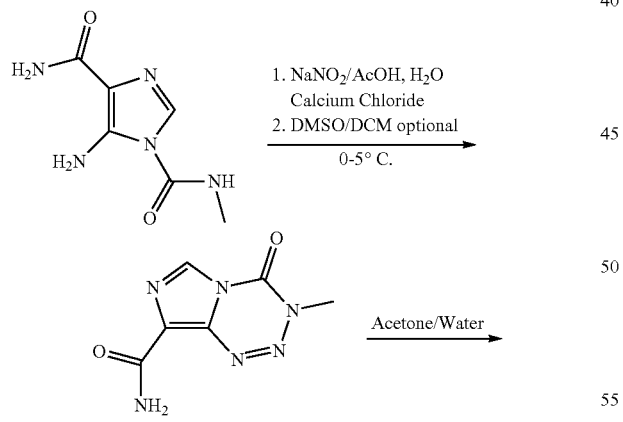

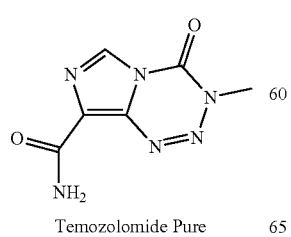

Temozolomide Pure

Acetic acid (135 ml, 2.36 mol.) was added to a suspension of 5-amino-N1methyl-1H-imidazole-1, 4-di Carboxamide (150 g, 0.82 mol.) and sodium nitrite (75 g, 1.09 mol.) in water (1500 ml) at −5 to 0° C. at such a rate so that temperature does not rise above 10° C. The reaction mixture was stirred at 0 to 5° C. for two hours and absence of starting material was checked by HPLC analysis. Ice bath was removed and powdered calcium chloride (375 g) was added in small lots to the reaction mass and the reaction mixture was stirred at 25-30° C. for 2 hours and cooled to −5 to 0° C. The reaction mixture was further stirred for 60 min, filtered and suck dried to give 113 g of impure Temozolomide, Dissolved impure Temozolomide in 375 ml DMSO and heat up to 60-70° C. and stirred for 30 min charged 15 g charcoal and stirred for 60 min and filter through hyflow bed and washed with 38 ml hot DMSO. Cooled DMSO solution up to 8-12° C. and stirred for 60 min. Filtered the material and washed with 50 ml chilled acetone sucker dried to get 85 g Temozolomide crude. Aqueous layer extracted with 5% DMSO in DCM 3750 ml×3 times. Combined organic layer and distilled out to get crude 15 g. Combined both crude 100 g and dissolved in Acetone water mixture (3:1) 2100 ml and stirred clear solution at 40-45° C. charged 15 g activated charcoal and stirred for 30 min. Filter through hyflow bed and cooled up to 0-5° C. filter the material after 1 hrs stirring and washed with chilled acetone 50 ml. Dried at 55-60° C. to get pure Temozolomide 23 g.

Purity (by HPLC): 99.9%.

While the present invention has been particularly described, persons skilled in the art will appreciate that many variations and modifications can be made. Therefore, the invention is not to be construed as restricted to the particularly described embodiments, examples and the scope and concept of the invention will be more readily understood by reference to the claims, which follow.

The invention claimed is:

1. A processor the preparation of Temozolomide of formula (VI):

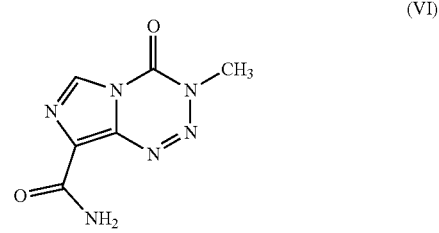

wherein the process comprises the following steps:

a) reacting a compound of formula (I):

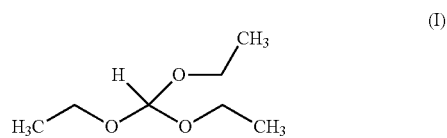

with a compound of formula (II):

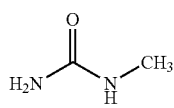

at a temperature in the range of 100° C. to 120° C., over a duration of time in the range of 4 hours to 10 hours, to provide a compound of formula (III):

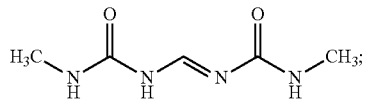

b) reacting the compound of formula (III) above with a compound of formula (IV):

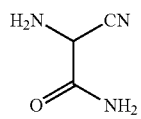

in the presence of (i) a non-alcoholic solvent selected from the group consisting of acetonitrile, dichloromethane, dichloroethane, and toluene, or a mixture thereof, and (ii) an inorganic acid selected from the group consisting of hydrochloric acid, nitric acid, and sulfuric acid, or a combination thereof, to provide a compound of formula (V):

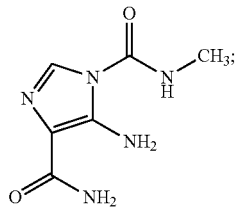

c) reacting the compound of formula (V) above with (i) (C1-C3) organic acid selected from the group consisting of formic acid, acetic acid, and propanoic acid, or a mixture thereof, and (ii) sodium nitrite, in the presence of aqueous medium, eta temperature in the range of −5° C. to 10° C., followed by the addition of (iii) a desiccant selected from the group consisting of sodium dithionate, sodium sulfate, barium chloride, and calcium chloride, in an amount in the ran of 20% w/w to 40% w/w with respect to the total amount of aqueous medium, to provide Temozolomide of the following formula:

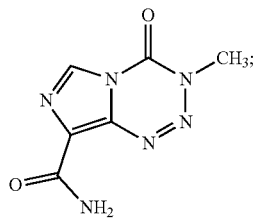 [SMILES: Cn1nnc2c(C(N)=O)ncn2c1=O]

and d) purifying the Temozolomide provided in step c) above in-situ with a 4% w/w to 10% w/w dimethyl sulfoxide solution in a halohydrocarbon solvent selected from the group consisting of dichloromethane, chloroform, and carbon tetrachloride, or a mixture thereof, to provide Temozolomide of formula (VI):

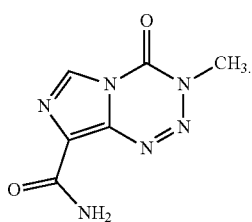

2. The process according to claim 1, wherein the non-alcoholic solvent is acetonitrile.

3. The process according to claim 1, wherein the inorganic acid is hydrochloric acid.

4. The process according to claim 1, wherein the (C1-C3) organic acid is acetic acid.

5. The process according to claim 1, wherein the desiccant is calcium chloride.

6. The process according to claim 1, wherein the halohydrocarbon solvent is dichloromethane.

* * * * *